United States Patent
Kho et al.

(10) Patent No.: US 10,454,901 B2
(45) Date of Patent: Oct. 22, 2019

(54) SYSTEMS AND METHODS FOR ENABLING DATA DE-IDENTIFICATION AND ANONYMOUS DATA LINKAGE

(71) Applicant: Health Data, Link Inc., Chicago, IL (US)

(72) Inventors: Abel Ngo Kho, Chicago, IL (US); Satyender Goel, Chicago, IL (US)

(73) Assignee: Datavant, Inc., San Francisco, CA (US)

( * ) Notice: Subject to any disclaimer, the term of this patent is extended or adjusted under 35 U.S.C. 154(b) by 734 days.

(21) Appl. No.: 15/000,905

(22) Filed: Jan. 19, 2016

(65) Prior Publication Data

US 2017/0208041 A1    Jul. 20, 2017

(51) Int. Cl.
| | |
|---|---|
| *G06F 21/62* | (2013.01) |
| *G16H 10/60* | (2018.01) |
| *H04L 29/06* | (2006.01) |
| *H04L 9/06* | (2006.01) |
| *H04L 9/32* | (2006.01) |
| *H04W 12/02* | (2009.01) |

(52) U.S. Cl.
CPC ...... *H04L 63/0428* (2013.01); *G06F 21/6254* (2013.01); *G16H 10/60* (2018.01); *H04L 9/0643* (2013.01); *H04L 9/3239* (2013.01); *H04W 12/02* (2013.01); *H04L 2209/42* (2013.01)

(58) Field of Classification Search
None
See application file for complete search history.

(56) References Cited

U.S. PATENT DOCUMENTS

| | | | |
|---|---|---|---|
| 2008/0109459 | A1 | 5/2008 | Trepetin |
| 2008/0120296 | A1* | 5/2008 | Kariathungal ......... G16H 10/60 |
| 2010/0042583 | A1 | 2/2010 | Gervais et al. |
| 2012/0041791 | A1 | 2/2012 | Gervais et al. |
| 2012/0151597 | A1 | 6/2012 | Gupta et al. |
| 2012/0266255 | A1 | 10/2012 | Gupta et al. |

(Continued)

FOREIGN PATENT DOCUMENTS

WO    2017/127560    7/2017

OTHER PUBLICATIONS

Anderson et al, Implementation of a deidentified federated data network for population-based cohort discovery, Aug. 2011, J Am Inform Assoc, 19, pp. e60-e67 (Year: 2011).*

(Continued)

*Primary Examiner* — Dennis W Ruhl
*Assistant Examiner* — William G Lultschik
(74) *Attorney, Agent, or Firm* — Polsinelli PC

(57) ABSTRACT

Aspects of the present disclosure describe systems and methods that dynamically de-identifies confidential and/or sensitive patient health data maintained at computing devices deployed within a communications network. A key value is securely transmitted from a remote device included in a first security domain to a first server included in a second security domain. Based on the key value, the first server accesses a dataset containing health records identifying individual patients and de-identifies all or part of the dataset. A second server included in a security domain different from the remote device and the first server matches the de-identified data to previously de-identified data and generates a unique alias identifier for the matched de-identified data.

18 Claims, 5 Drawing Sheets

(56) References Cited

U.S. PATENT DOCUMENTS

2015/0128284 A1    5/2015  LaFever et al.
2015/0128285 A1    5/2015  LaFever et al.
2016/0147945 A1*   5/2016  MacCarthy ......... G06F 21/6254
                                                        705/51

OTHER PUBLICATIONS

International Searching Authority, International Search Report and Written Opinion, issued for PCT Application No. PCT/US2017/014155, dated Apr. 6, 2017 (13 pages).

* cited by examiner

| | | | | | | |
|---|---|---|---|---|---|---|
| 402 — A | H#1 | H#2 | H#3 | H#4 | --- . | H#18 |
| 404 — B | H#1 | H#2 | H#3 | H#4 | --- . | H#18 |
| 406 — C | H#1 | H#2 | H#3 | H#4 | --- . | H#18 |
| 408 — D | H#1 | H#2 | H#3 | H#4 | --- . | H#18 |
| --- | | | | | | |
| 410 — N | H#1 | H#2 | H#3 | H#4 | --- . | H#18 |

400

| | | | | | | | >1 — 424 |
|---|---|---|---|---|---|---|---|
| 402A — A | x | H#2 | H#3 | H#4 | --- . | H#18 | .060 |
| 404A — B | H#1 | H#2 | H#3 | H#4 | --- . | H#18 | .201 |
| 406A — C | H#1 | x | x | x | --- . | x | 1.06 |
| 408A — D | H#1 | H#2 | x | H#4 | --- . | H#18 | .030 |
| --- | | | | | | | |
| 410A — N | H#1 | H#2 | x | H#4 | --- . | x | .700 |
| 422 — P | H#1 | H#2 | H#3 | H#4 | --- . | H#18 | .700 |

SYSTEMS AND METHODS FOR ENABLING DATA DE-IDENTIFICATION AND ANONYMOUS DATA LINKAGE

TECHNICAL FIELD

Aspects of the present disclosure relate to the de-identifying of sensitive data while preserving data usability across software applications.

BACKGROUND

Modern computing has improved the quality of health care by enabling interested parties to instantly retrieve and access patient health care data and related information and enable the rapid exchange of such patient health care data between a larger number of people who can contribute to the care and treatment of a patient. Such technology has also increased the risk of unauthorized use, access and disclosure, of confidential health care data. Moreover, various healthcare regulations require confidential data be handled in a specific way. Thus, confidential health data is not utilized to its full potential to support effective and efficient care. Balancing patient privacy protections with efforts to advance data-driven medical and/or clinical research is an ongoing challenge for many healthcare organizations and the larger health care industry. It is with these observations in mind, among others, that various aspects of the present disclosure were developed.

SUMMARY

Aspects of the present disclosure include methods, systems, and computer readable mediums for dynamically de-identifying data from a data source. The methods, systems, and computer readable mediums involve a remote device deployed in a first security domain of a communications network, the remote device for generating a key value corresponding to a project requiring de-identification of data. The methods, systems, and computer readable mediums further involve a first server located in a second security domain of the communications network. The first server is configured to: securely receive the key value from the remote device and in response to receiving the key value: access a dataset maintained at the first server, the dataset including at least one individual record that uniquely identifies an individual. The first server is further configured to de-identify the dataset so that the at least one individual record in the dataset no longer uniquely identifies the individual.

In some embodiments, the methods, systems, and computer readable mediums include a second server located in a third security domain of the communications network to: automatically match the de-identified dataset with previously de-identified data to generate a universal de-identified dataset. The second server is further configured to, when a match occurs, automatically generate a unique and anonymous identifier for the universal de-identified dataset.

BRIEF DESCRIPTION OF THE DRAWINGS

The foregoing and other objects, features, and advantages of the present disclosure set forth herein will be apparent from the following description of particular embodiments of those inventive concepts, as illustrated in the accompanying drawings. Also, in the drawings the like reference characters refer to the same parts throughout the different views. The drawings depict only typical embodiments of the present disclosure and, therefore, are not to be considered limiting in scope.

FIG. 4 is a block diagram of a weighting algorithm, according to aspects of the present disclosure.

DETAILED DESCRIPTION

Aspects of the present disclosure describe systems and methods that dynamically de-identify confidential and/or sensitive patient health data, such as protected health information ("PHI") and/or personally identifiable information ("PII"), maintained at various computing devices deployed within a communications network. In various aspects, a graphical-user interface, web portal, and/or the like (referred to collectively as a "Portal"), located within its own security domain, enables users to securely obtain an encrypted seed and/or key value that is used in a method to provide users with the ability to create de-identified hashes on portions of confidential and/or sensitive patient health data (e.g., PHI and/or PII). Subsequently, one or more de-identification protocols and/or algorithms may be executed by a server located within a different security domain than the Portal. The server de-identifies the identified portions of confidential and/or sensitive patient health data (e.g., PHI and/or PII) and generates a series of corresponding unique identifiers that uniquely identifies the de-identified data, wherein the identifier is different than any personal health identifiers originally included in the initial set of confidential and/or sensitive patient health data (e.g., PHI and/or PII), thereby ensuring that no specific patients can ever be individually identified via the use of the series of unique identifiers.

In some embodiments, the newly de-identified data may be linked to previously de-identified data, thereby anonymously linking the data to a single, unidentifiable, patient entity represented within the de-identified data, as will be described in further detail below. In such embodiments, a weighting algorithm may be executed that matches the de-identified data to the previously de-identified data. All of the matched de-identified data is then automatically assigned a universal patient ID that uniquely identifies the set of matched data. Subsequently, the data may be processed and/or otherwise analyzed to generate various medical analytics, perform research, and/or the like. While the previous example refer to patient health care data, it is contemplated that the various mechanisms, processes, and/or systems may be used in other contexts, and applied to and upon other types of data and datasets.

Figure 1:
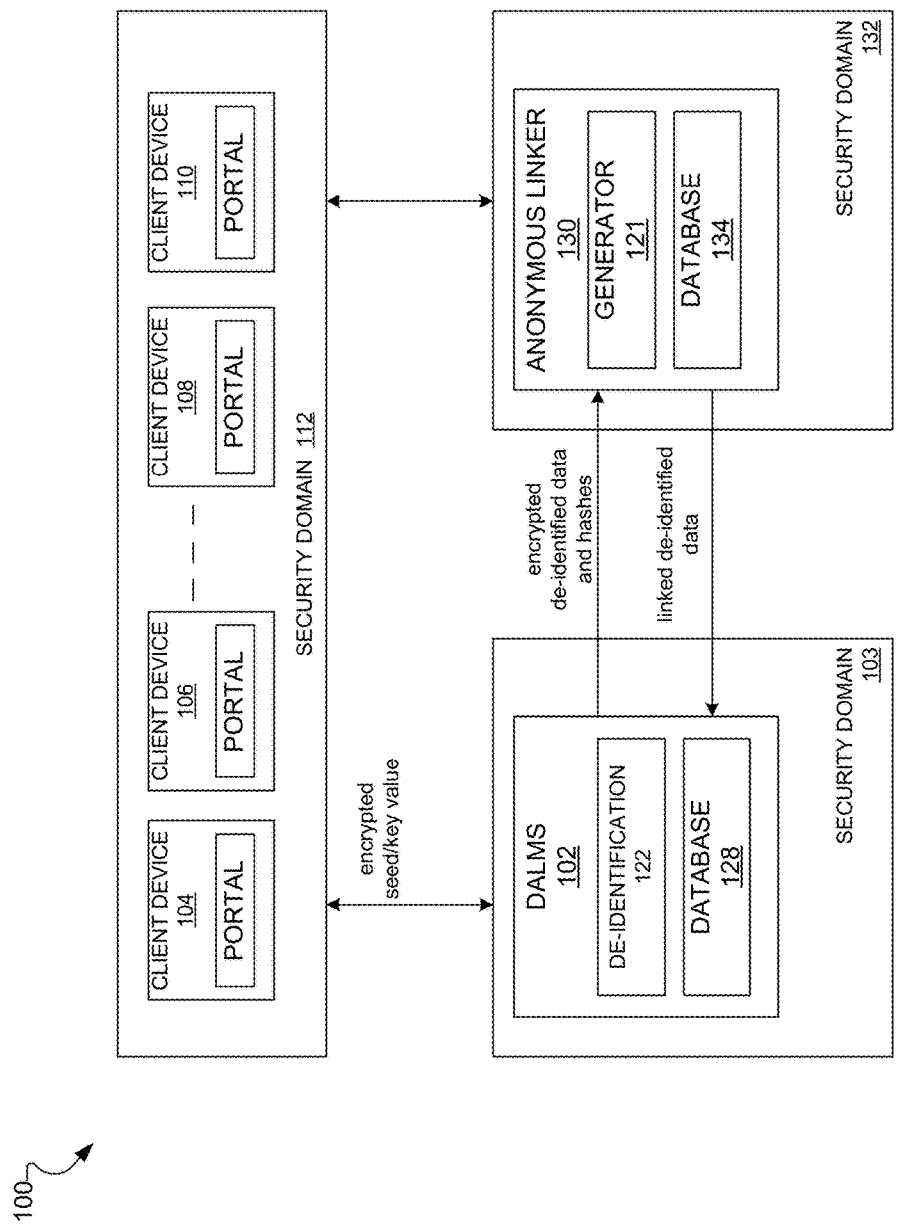
FIG. 1 is a block diagram illustrating a computing architecture for de-identifying and/or anonymously linking confidential patient health care data, according to aspects of the present disclosure.

FIG. 1 illustrates an example communications network 100 comprising a de-identification and anonymous linkage management system 102 ("DALMS") for de-identifying confidential and/or sensitive patient health data (e.g., PHI and/or PII). The communications network 100 may be an IP-based telecommunications network, the Internet, an intranet, a local area network, a wireless local network, a content distribution network, or any other type of communications network, as well as combinations of networks. For example, in one particular embodiment, the communications network 100 may be a telecommunications network including fiber-optic paths between various network elements, such as servers, switches, routers, and/or other optical telecommunications network devices that interconnect to enable receiving and transmitting of information between the various elements as well as users of the network.

According to one embodiment, the DALMS 102 may be a server located within its own domain and/or security domain 103. Generally speaking, a security domain is a classification of computing components that all trust a common security token for authentication, authorization or session management. The DALMS 102 represents the various computing systems, services, applications, and/or processes that may be deployed at a healthcare enterprise, and thus, may include large data sets of confidential and/or sensitive patient health data (e.g., PHI and/or PII). For example, in one embodiment, the DALMS 102 may include PHI and/or PII information for a plurality of medical patients, or other confidential patient health care data, which includes any information in the medical record or designated record set that can be used to identify an individual and that was created, used, or disclosed in the course of providing a health care service such as diagnosis or treatment. The DALMS 102 may include a de-identification module 122 to de-identify portions of the confidential and/or sensitive patient health data (e.g., PHI and/or PII). In some embodiments, the DALMS 102 may include a database 128 for storing and retrieving the de-identified data. Although the database 128 of FIG. 1 is depicted as being located within DALMS 102, it is contemplated that the database 128 may be located external to the DALMS 102, such as at a remote location, and may securely communicate with the DALMS 102.

One or more client devices 104-110 may securely transmit confidential and/or sensitive patient health data (e.g., PHI and/or PII) (e.g., via Secure Shell) to the DALMS 102, and vice versa. As with the DALMS 102, the one or more client devices 104-110 are included within their own security domain 112. In some embodiments, the one or more client devices 104-110 may service the need of users interested de-identifying data maintained the DALMS 102. To do so, a user may interact with the one or client devices 104-110 and provide input, which may be processed by the de-identification module 122 of the DALMS 102 to de-identify the data. For example, if a user were interested in de-identifying data for a particular project, as will be further explained below, a user may interact with the one or more client devices 104-110 to provide data including a seed value and/or key value that identifies the relevant project, and which may be processed by the de-identification module 122 of the DALMS 102. In one embodiment, each of the one or more client devices 104-110 may include a processor-based platform that operates on any suitable operating system, such as Microsoft® Windows®, Linux®, and/or the like that is capable of executing software.

In some embodiments, the DALMS 102 may communicate with an anonymous linker 130 that may be located within its own security domain 132. As will be described in further detail below, the anonymous linker 130 may employ a generator 121 to link patient health data (e.g., PHI and/or PII) that has been newly de-identified by the DALMS 102, with patient health data (e.g., PHI and/or PII) that was previously de-identified and currently being maintained at the anonymous linker 130, such as for example in a database 134. Stated differently, maintained in the database 134 of the anonymous linker 130 is patient health data (e.g., PHI and/or PII) that has already been de-identified. Thus, no individual users can be identified from the data. When new data is de-identified by the DALMS 102, the newly de-identified data is combined and/or otherwise matched with the already existing de-identified data to ensure there is no duplicate data. A unique "universal" identifier is then provided for the matched de-identified data, thereby uniquely identifying the data without actually identifying a specific health care patient. The anonymous linker 130 may be any of, or any combination of, a: personal computer; handheld computer; mobile phone; digital assistant; smart phone; server; application; and the like. Although the database 134 is depicted as being located within the anonymous linker 130, it is contemplated that the database 134 may be located external to the anonymous linker 130, such as at a remote location, and may securely communicate with the anonymous linker 130.

In some embodiments, the security domain 103, the security domain 112, and the security domain 132 represent separate sets and/or networks of computing components and/or devices and cannot be accessed without proper authentication and/or encryption/decryption. Thus, the DALMS 102 and any data of the security domain 103 may not be directly accessed by one or more client devices 104-110 located within in the security domain 112 or the anonymous linker 130 located within the security domain 132, without proper authentication and/or encryption/decryption. The one or more client devices 104-110 and any data located within in the security domain 112 may not be directly accessed the DALMS 102 of the security domain 103 or the anonymous linker 130 located within the security domain 132, without proper authentication and/or encryption/decryption. The anonymous linker 130 and any data located within in the security domain 132 may not be directly accessed the DALMS 102 of the security domain 103 or the one or more client devices 104-110 located within the security domain 112, without proper authentication and/or encryption/decryption.

Figure 2:
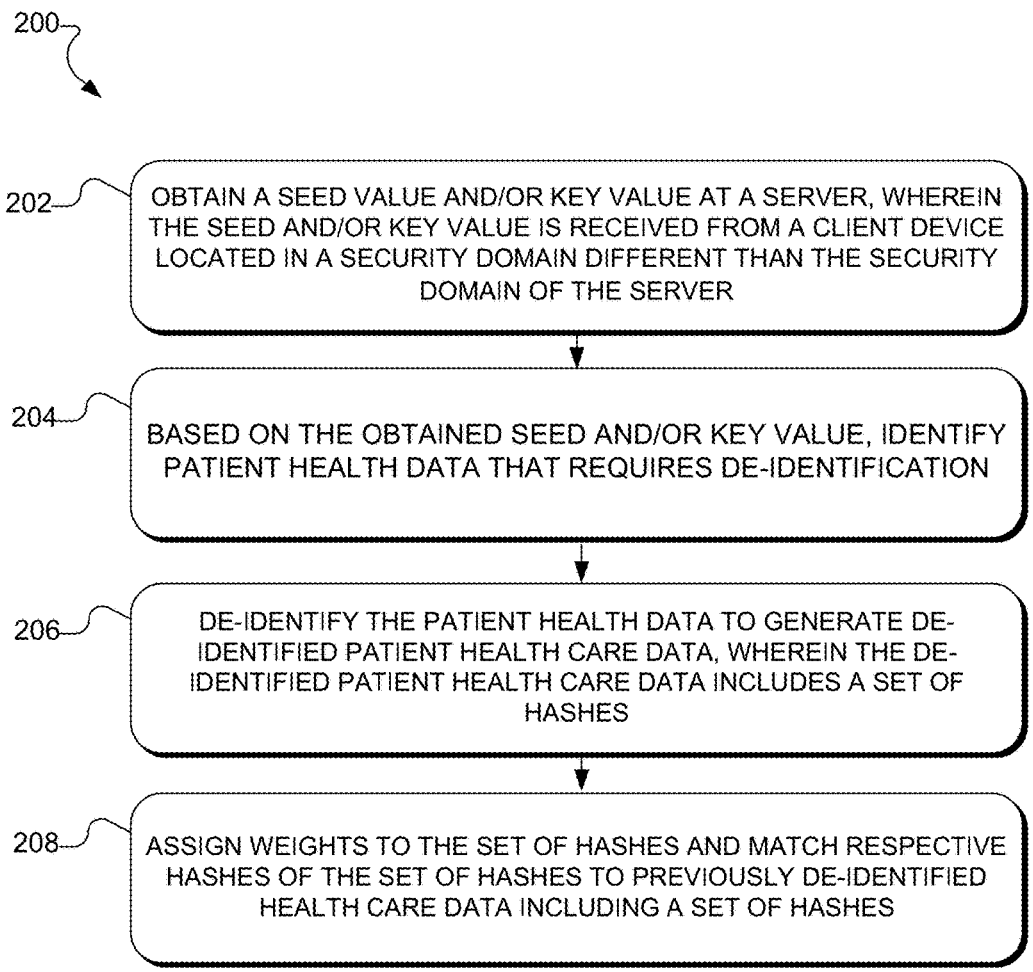
FIG. 2 is a flowchart illustrating an example process for de-identifying data and/or anonymously linking (e.g., matching) de-identified data is provided, according to aspects of the present disclosure.

Referring now to FIG. 2 and with general reference to FIG. 1, an illustrative process 200 for de-identifying data and anonymously linking (e.g., matching) the de-identified data with previously de-identified data is provided. As illustrated, process 200 begins with obtaining a key value and/or seed value at a server, wherein the seed/key value is received from a remote device located in a security domain that is different than the security domain in which the server device is located (operation 202). Referring to FIG. 1, the one or more client devices 104-110, located in the security domain 112, may securely transmit a key value or seed value to the DALMS 102, which processes the seed/key value to determine or otherwise identify a portion of patient health data (e.g., PHI and/or PII) that requires de-identification. In one embodiment, the DALMS 102 is located in security domain 103, which is different than the security domain 112.

In some embodiments, a graphical user-interface (e.g., a web interface) may be generated and/or initialized at the one or more client devices 104-110 that may be employed to deliver an encrypted, project-based, seed/key value to the DALMS 102. For example, a graphical user-interface or command line application may be initialized at the client devices 104-110 that allows a user to request the seed/key value assigned to particular project, and for which a user is approved to access. More specifically, the user credentials are attached and pre-assigned to one or more projects and stored at the web portal, and may be used to retrieve the relevant seed/key value for a given project and the applicable patient health data (e.g., PHI and/or PII).

Figure 3A:
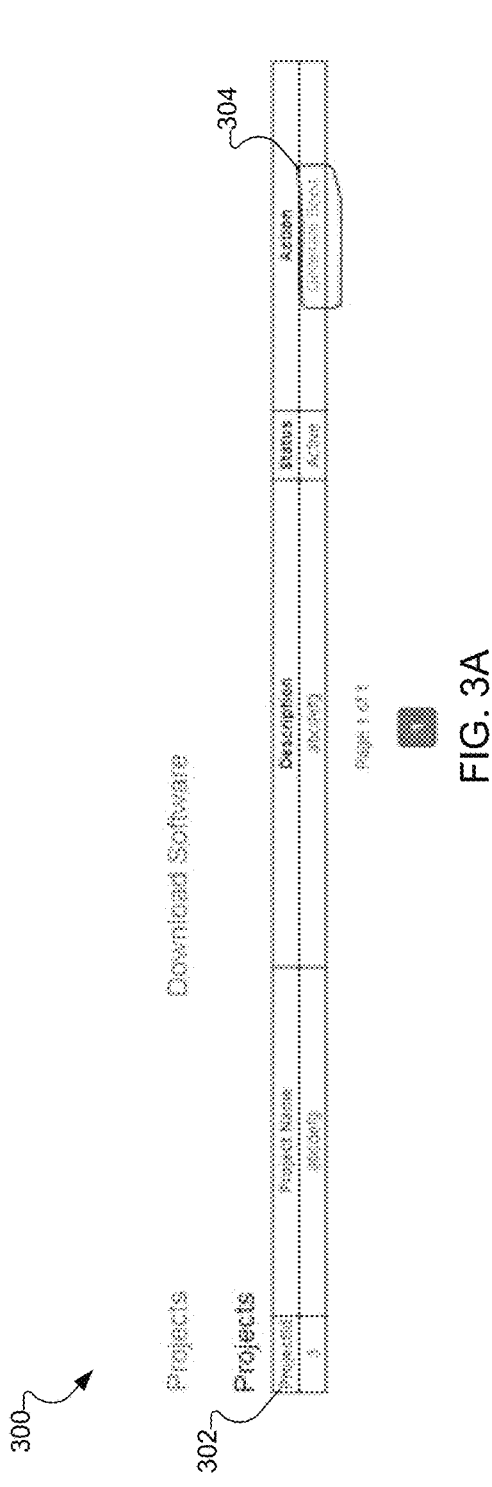
FIGS. 3A-3B are block diagrams illustrating a graphical user-interface, according to aspects of the present disclosure.
Figure 3B:
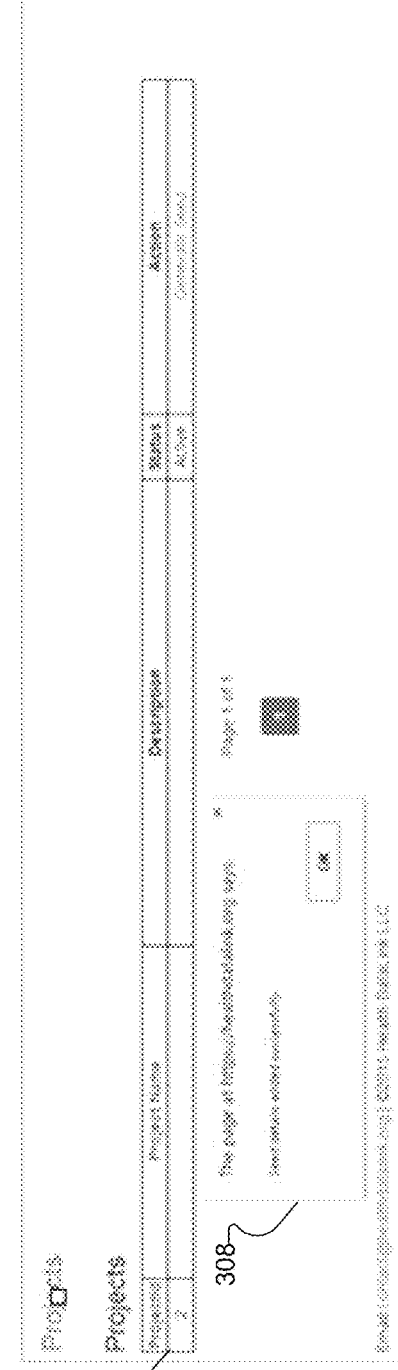

FIGS. 3A and 3B provide example screen shots of graphical user-interface(s)/web portal(s) that may be generated at the one or more client devices 1-4-110. As illustrated, the graphical user-interface may provide various components, buttons, menus, and/or other functions to allow a user to request the seed/key value. For example, a user may provide authentication information, such as a username and password, and information describing a particular project. Once a user has provided the proper login credentials in, an interface 300 may be generated that enables the user to select or otherwise identify a project 302 and generate a seed 304 corresponding to the project 302. In response, an interface 306 may be generated signaling that a seed has been generated for the project 302 (illustrated at 308). Each seed or key is unique to each project and each user needs to be approved and assigned to a project before using the de-identification application installed at a source/client end. In some embodiments, a single user may be assigned to more than one project, the user may be able to select project list from the de-identification graphical user interface or provide project details to the command line application for requesting the relevant seed/key.

In response, the graphical-user-interface/web portal, may encrypt the seed/key value and transmit the seed/key value over a secured protocol to de-identification application at source/client end (e.g., client devices 104-110). For example and in one embodiment, the seed value and/or key value may be encrypted using Secure Hash Algorithms, such as for example SHA-512. Subsequently, the encrypted seed value and/or key value securely transmitted to the DALMS 102, which, as illustrated in FIG. 1, is located within its own security domain inside the communications network 100.

Referring again to FIG. 2, the seed/key value is decrypted (if necessary) and used to process patient health data (e.g., PHI and/or PII) requiring de-identification (operation 204). Referring to FIG. 1, the DALMS 102 processes the seed value in combination with other PHI/PII elements to generate hashes via cryptographic algorithms, such as SHSA-512. In one embodiment, the confidential patient data (e.g., PHI and/or PII) identified for de-identification by the project specifications may include a series of records corresponding to individual health patients. For example, typical individual records included in the data may include a plurality of fields, such as name and birth date, residential address, ethnic background, sex, social security number, etc., all of which, when considered (e.g., analyzed) together, may be used to uniquely identify a user. Each record may also include various fields related to the medical circumstances of the individual, or fields characterizing the individual's health, health status, and/or the like. For example, the fields may identify any medications to which the user is currently prescribed, diseases associated with the user, among others.

Referring again to FIG. 2, the patient health data (e.g., PHI and/or PII) obtained for de-identification is de-identified to generate de-identified patient health data (e.g., PHI and/or PII) (operation 206). In one embodiment and with reference to FIG. 1, the DALMS 102 initiates the de-identification module 122 that executes a de-identification algorithm that de-identifies the data. More specifically, the de-identification algorithm removes any personal data and/or unique patient identifying data fields from the obtained health data, such that an individual patient can no longer be individually and uniquely identified from the data.

In one embodiment, to de-identify the patient health data (e.g., PHI and/or PII), the de-identification module 122 may generate a bundle or set of one or more different hashes, based on the patient health data elements, such as the patient health elements of the PHI and the PII. More specifically, six (6) variables (or any number of variables) may be selected from the patient health data identified for de-identification, such as name, date of birth, social-security number, address, gender, ethnicity, and/or the like. The identified variables may then be processed using SHA-512 functions (or other cryptographic functions) to generate the number of different hashes (18 shown as an example). Additionally, for each set of generated hashes (18 in the illustrated embodiment), a unique, non-repeatable, identifier is generated. As an example, assume two different sets of 18 hashes are generated for two different sets of patient health data (e.g., PHI and/or PII) corresponding to two different projects, Project A and Project B. A set of 18 hashes, "set 1" may be generated for Project A and a set of 18 hashes, "set 2", may be generated for Project B. Additionally, in some embodiments, a unique identifier uniquely identifying the "set 1" of hashes is generated and a unique identifier uniquely identifying the "set 2" of hashes is generated. Each set of hashes and its corresponding unique identifier is encrypted and stored as a bundle, for example in the database 128, or elsewhere.

Each unique id generated for each set of hashes may be maintained in a 1×1 look-up table ("LUT") stored within the database 128 of the DALMS 102. In one embodiment, the look-up table may contain the source/client side patient ID (any id used to identify patient in local system, for example medical record number etc.) with a unique non-derived hashed id generated by de-identification application for each patient. This unique ID is also passed along with Hash bundles to get stored in the database 128, which may be used to re-identify patients at source/client end (e.g., within security domain 112). The unique ID (hash ID) is unique for any number of patients for each project across any number of sources/clients (e.g., client devices 104-110) using the same seed/key. The uniqueness is maintained by passing on an alphanumeric key (for example a 5 digit long key with combination of a-z, A-Z, 0-9 characters (case sensitive)) for each request (different alphanumeric key is generated, the record of each is kept at web portal). This alphanumeric key along and the local time stamp at the sources get encrypted via cryptographic method (like SHA 512) executed by the de-identification module 122 and generate a unique 128 bit hash ID for each patient/record.

As illustrated in FIG. 2, after the data has been de-identified, the newly de-identified data is compared or otherwise matched to previously de-identified data (e.g., de-identified data from another source) to determine whether any anonymous links can be established (operation 208). Referring to FIG. 1, the DALMS 102 transmits the encrypted sets of hashes to the anonymous linker 130. The anonymous linker 130 matches the newly de-identified data to previously de-identified data to determine whether there is a match. Initially, the anonymous linker 130 may require user authentication similar to the process described above, when a user is accessing a seed and/or key value. Then, upon proper authentication, the anonymous linker 130 may execute a weighting algorithm that anonymously links the newly de-identified data with the previously de-identified data. Stated differently, each set of hashes generated by the DALMS 102 is compared to all other existing set of hashes to determine whether a match exists.

The weighting algorithm is executed to assign weights to hashes included in a given set of hashes based on the characteristics of the population attributes on which the weights are being applied. For example, if a social security number is included in the set of variables used to generate the hash, the weighted value may be higher (if matched with the same hash of the other pair) than if a "name" variable is used to generate the hash. In some embodiments, hash's weights remains the same within the project and don't change to allow consistent matching to occur.

Once the hashes are weighted, the hashes are matched. FIG. 4 illustrates an example of matching between sets of hashes, according to one embodiment. As illustrated, sets 402-410 of table 400 each include 18 hashes (illustrated as H#1, H32, H#3, and so on). For each hash corresponding to each set of hashes, there is a weight value assigned for each match (represented by 'x') and summed for each record. For example, in the illustrated embodiment, H#1 of hash set 402 to 410 may include a weighted value of 0.10. H#2 of hash set 402-410 may include a weighted value of 0.030. H#4 of hash set 402-410 may include a weighted value of 0.90, and so on. All 18 hash values corresponding to set 402-410 may include an associated weighted value. The case is the same for all other set of hashes. Thus, in one embodiment, all 18 hashes for hash sets 404-410 will include an individual weighted value.

The weighted values of each hashed 'when-matched' set are compared to all other previously de-identified and hashed data to determine whether there is a match. Table 420 of FIG. 4 illustrates an example of matching hashes. In the illustrated embodiment, all of the hash sets 402-410 are being compared and/or otherwise matched to pre-existing de-identified and hashed dataset P 422. Hash set 402A shows provides an "x" at H#1 indicating that H#1 of hash set 402 matches with H#1 of pre-existing de-identified and hashed dataset P 422. Hash set 406A provides an "x" at H#2, H#3, and H#4, indicating that H#2, H#3, and H#4 of hash set 406A matches with H#2, H#3, and H#4 of pre-existing de-identified and hashed dataset P 422. Hash set 410A shows provides an "x" at H#3 and H#18 indicating that H#3 and H#18 of hash set 410A matches with H#3 and H#18 of pre-existing de-identified and hashed dataset P 422.

In one embodiment, all of the matched weighted values for a given hash set are added into a quantitative value and compared to a threshold that signals that the matched set of hashes represent the same patient health data (e.g., PHI and/or PII). In one embodiment, the threshold represents a value or level chosen that indicates a likelihood of a 100% match between two records. The threshold value may be established based on population characteristics, such as demographics, availability of attributes or data points, etc. In another embodiment, the matching threshold may be established by benchmarking a real population data set of 1 million or more unique patients against another known patient registry of ten thousand or more records, such that matches between the two sets achieve 100% specificity. Different patient identifiers are assigned different scores (e.g. a hash of the social security number might be assigned a score of 0.7, a hash of the last name might be assigned a score of 0.2, and a hash of date of birth might be assigned a score of 0.2). If all three hashes are the same for a single patient, then the match score for this patient would be 0.7+0.2+0.2 or 1.1. The threshold score was set (e.g. in this instance scores >1.0) such that scores over the value of 1 correlate with a match likelihood of 100%. Accordingly, the threshold may be adjusted based on the availability of population specific demographic features.

In the illustrated embodiment, if the value is greater than 1, as illustrated at 424, then the hash set is considered to represent the same patient represented by the previously de-identified data of hash set P 422. Thus, since the weighted value of 406A is greater than 1, the hash set D for 406A and 422 P are considered to correspond to the same health care patient and the datasets are combined.

All combined datasets are provided with an associated "universal" identifier that uniquely identifies the hashed data sets as a single set of identifiable health patient data that corresponds to one individual, without actually identifying a unique individual healthcare patient. Thus, the anonymous linker 130 allows for aggregation of the de-identified health data in an efficient manner, such that there are no duplicate entries and identical patient data is combined into a single record. By linking such medial information at the patient level—without exposing the actual identity of the user, new research, testing, and observations can be made.

Figure 5:
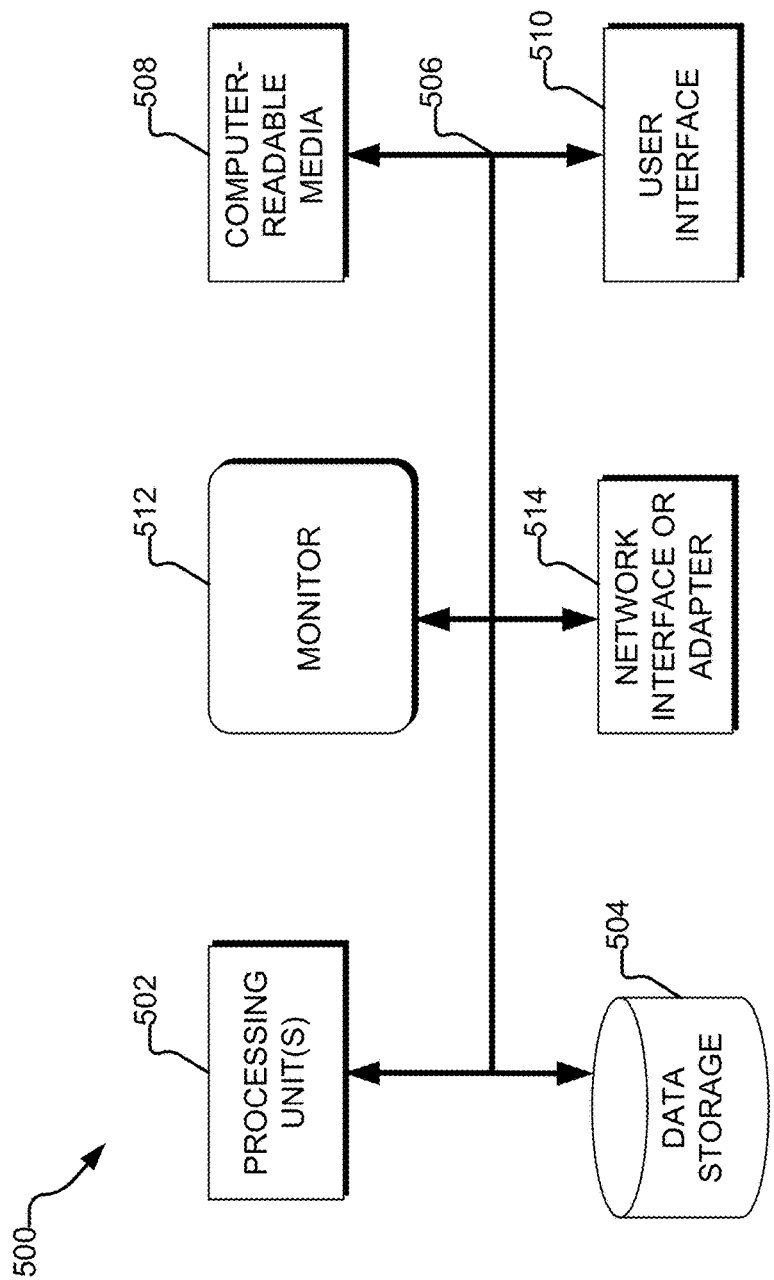
FIG. 5 is a block diagram illustrating a computing device for de-identifying data and/or anonymously linking (e.g., matching) de-identified data, according to aspects of the present disclosure.

FIG. 5 illustrates an example of a suitable computing and networking environment 500 that may be used to implement various aspects of the present disclosure described in FIGS. 1-3A and 3B. As illustrated, the computing and networking environment 500 includes a general purpose computing device 500, although it is contemplated that the networking environment 500 may include one or more other computing systems, such as personal computers, server computers, hand-held or laptop devices, tablet devices, multiprocessor systems, microprocessor-based systems, set top boxes, programmable consumer electronic devices, network PCs, minicomputers, mainframe computers, digital signal processors, state machines, logic circuitries, distributed computing environments that include any of the above computing systems or devices, and the like.

Components of the computer 500 may include various hardware components, such as a processing unit 502, a data storage 504 (e.g., a system memory), and a system bus 506 that couples various system components of the computer 500 to the processing unit 502. The system bus 506 may be any of several types of bus structures including a memory bus or memory controller, a peripheral bus, and a local bus using any of a variety of bus architectures. For example, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computer 500 may further include a variety of computer-readable media 508 that includes removable/non-removable media and volatile/nonvolatile media, but excludes transitory propagated signals. Computer-readable media 508 may also include computer storage media and communication media. Computer storage media includes removable/non-removable media and volatile/nonvolatile media implemented in any method or technology for storage of information, such as computer-readable instructions, data structures, program modules or other data, such as RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information/data and which may be accessed by the computer 500. Communication media includes computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. For example, communication media may include wired media such as a wired network or direct-wired connection and wireless media such as acoustic, RF, infrared, and/or other wireless media, or some combination thereof. Computer-readable media may be embodied as a computer program product, such as software stored on computer storage media.

The data storage or system memory 504 includes computer storage media in the form of volatile/nonvolatile memory such as read only memory (ROM) and random access memory (RAM). A basic input/output system (BIOS), containing the basic routines that help to transfer information between elements within the computer 500 (e.g., during start-up) is typically stored in ROM. RAM typically contains data and/or program modules that are immediately accessible to and/or presently being operated on by processing unit 502. For example, in one embodiment, data storage 504 holds an operating system, application programs, and other program modules and program data.

Data storage 504 may also include other removable/non-removable, volatile/nonvolatile computer storage media. For example, data storage 504 may be: a hard disk drive that reads from or writes to non-removable, nonvolatile magnetic media; a magnetic disk drive that reads from or writes to a removable, nonvolatile magnetic disk; and/or an optical disk drive that reads from or writes to a removable, nonvolatile optical disk such as a CD-ROM or other optical media. Other removable/non-removable, volatile/nonvolatile computer storage media may include magnetic tape cassettes, flash memory cards, digital versatile disks, digital video tape, solid state RAM, solid state ROM, and the like. The drives and their associated computer storage media, described above and illustrated in FIG. 5, provide storage of computer-readable instructions, data structures, program modules and other data for the computer 500.

A user may enter commands and information through a user interface 510 or other input devices such as a tablet, electronic digitizer, a microphone, keyboard, and/or pointing device, commonly referred to as mouse, trackball or touch pad. Other input devices may include a joystick, game pad, satellite dish, scanner, or the like. Additionally, voice inputs, gesture inputs (e.g., via hands or fingers), or other natural user interfaces may also be used with the appropriate input devices, such as a microphone, camera, tablet, touch pad, glove, or other sensor. These and other input devices are often connected to the processing unit 502 through a user interface 510 that is coupled to the system bus 506, but may be connected by other interface and bus structures, such as a parallel port, game port or a universal serial bus (USB). A monitor 512 or other type of display device is also connected to the system bus 506 via an interface, such as a video interface. The monitor 512 may also be integrated with a touch-screen panel or the like.

The computer 500 may operate in a networked or cloud-computing environment using logical connections of a network interface or adapter 514 to one or more remote devices, such as a remote computer. The remote computer may be a personal computer, a server, a router, a network PC, a peer device or other common network node, and typically includes many or all of the elements described above relative to the computer 500. The logical connections depicted in FIG. 5 include one or more local area networks (LAN) and one or more wide area networks (WAN), but may also include other networks. Such networking environments are commonplace in offices, enterprise-wide computer networks, intranets and the Internet.

When used in a networked or cloud-computing environment, the computer 500 may be connected to a public and/or private network through the network interface or adapter 514. In such embodiments, a modem or other means for establishing communications over the network is connected to the system bus 506 via the network interface or adapter 514 or other appropriate mechanism. A wireless networking component including an interface and antenna may be coupled through a suitable device such as an access point or peer computer to a network. In a networked environment, program modules depicted relative to the computer 500, or portions thereof, may be stored in the remote memory storage device.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the disclosure and are thus within the spirit and scope of the present disclosure. From the above description and drawings, it will be understood by those of ordinary skill in the art that the particular embodiments shown and described are for purposes of illustrations only and are not intended to limit the scope of the present disclosure. References to details of particular embodiments are not intended to limit the scope of the disclosure.

What is claimed is:

1. A system for dynamically de-identifying data from a data source comprising:
    a remote device deployed in a first security domain of a communications network, the remote device for generating a key value corresponding to a project requiring de-identification of data;
    a first server located in a second security domain of the communications network different than the first security domain, the first server to:
        securely receive the key value from the remote device; and
        in response to receiving the key value:
            access a dataset maintained at the first server, the dataset including a record including data that uniquely identifies an individual;
            generate a de-identified dataset from the dataset by removing the data that uniquely identifies the individual from the record; and
            generate a hash based on the removed data; and
    a second server located in a third security domain of the communications network different than each of the first security domain and the second security domain, the second server to:
        securely receive the hash from the first server;
        automatically match the de-identified dataset with a previously de-identified dataset by comparing the hash based on the removed data to a hash associated with the previously de-identified data; and
        in response to automatically matching the de-identified dataset with a previously de-identified dataset, automatically generate a universal de-identified data set by providing a unique identifier for the universal de-identified dataset to each of the de-identified dataset and the previously de-identified dataset,
    wherein the remote device requires proper authentication or encryption to access the first server.

2. The system of claim 1, wherein to generate the de-identified dataset includes:
    generating a first set of hashes including multiple hashes corresponding to the dataset based on characteristics of the individual, the multiple hashes including the hash based on the removed data.

3. The system of claim 2, wherein to automatically match the de-identified dataset includes:
generating a weight value for respective hashes of the multiple hashes;
calculating a total weight by comparing the first set of hashes to a second set of hashes associated with the previously de-identified dataset and summing the weight value for each hash of the first set of hashes that matches a hash of the second set of hashes; and
identifying the match in response to the total weight being more than a threshold.

4. The system of claim 2, wherein to generate the de-identified dataset further includes generating a unique hash identifier that identifies the multiple hashes as the first set of hashes.

5. The system of claim 1, wherein the remote device is further configured to encrypt the key value and transmit the encrypted key value to the first server, in response to user input, at the remote device, requesting access to the project requiring the de-identification of data.

6. The system of claim 1, wherein the dataset includes health data, wherein the record is a protected health information record, and wherein the individual is a health patient.

7. A method for dynamically de-identifying data from a data source comprising:
at a first server within a first security domain:
securely receiving, at the first server and from a remote device in a second security domain different than the first security domain, a key value from the remote device;
in response to receiving the key value at the first server:
accessing a dataset maintained at the first server, the dataset including a record that uniquely identifies an individual;
generating a de-identified dataset from the dataset by removing the data that uniquely identified the individual from the record; and
generating a hash based on the removed data; and
at a second server within a third security domain different than each of the first security domain and the second security domain:
securely receiving the hash from the first server;
automatically matching the de-identified dataset with a previously de-identified dataset by comparing the hash based on the removed data to a hash associated with the previously de-identified data; and
in response to automatically matching the de-identified dataset with the previously de-identified dataset, automatically generating a universal de-identified data set by providing a unique identifier for the universal de-identified dataset to each of the de-identified dataset and the previously de-identified dataset,
wherein the first server requires proper authentication or encryption to access the second server.

8. The method of claim 7, wherein de-identifying the dataset comprises:
generating a first set of hashes including multiple hashes corresponding to the dataset based on characteristics of the individual, the multiple hashes including the hash based on the removed data.

9. The method of claim 8, wherein automatically matching the de-identified dataset comprises:
generating a weight value for respective hashes of the multiple hashes;
calculating a total weight by comparing the first set of hashes to a second set of hashes associated with the previously de-identified dataset and summing the weight value for each hash of the first set of hashes that matches a hash of the second set of hashes; and
identifying the match when the total weight is more than a threshold.

10. The method of claim 8, further comprising generating a unique hash identifier that identifies the multiple hashes as the first set of hashes.

11. The method of claim 7 further comprising encrypting the key value at the remote device and transmitting the encrypted key value to the first server in response to receiving user input at the remote device, requesting access to a project requiring the de-identification of data.

12. The method of claim 7, wherein the dataset includes health data, wherein the record is a protected health information record, and wherein the individual is a health patient.

13. A non-transitory computer readable medium including executable instructions for dynamically de-identifying data from a data source, the instructions comprising:
first instructions executable by a processor of a first server, such that, when executed by the processor of the first server, the instructions cause the processor of the first server to:
securely receive a key value from the remote device;
in response to receiving the key value:
access a dataset maintained by the first server, the dataset including a record that uniquely identifies an individual;
generate a de-identified dataset from the dataset by removing the data that uniquely identified the individual from the record; and
generate a hash based on the removed data; and
second instructions executable by a processor of a second server, such that, when executed by the processor of the second server, the instructions cause the processor of the second server to:
securely receive the hash from the first server;
automatically match the de-identified dataset with a previously de-identified dataset by comparing the hash based on the removed data to a hash associated with the previously de-identified data; and
when a match occurs, automatically generate a universal de-identified data set by providing a unique identifier for the universal de-identified dataset to each of the de-identified dataset and the previously de-identified dataset
wherein the first server requires proper authentication or encryption to access the second server.

14. The non-transitory computer readable medium of claim 13, wherein the first instructions further cause the processor of the first server to de-identify the dataset by:
generating a first set of hashes including multiple hashes corresponding to the dataset based on characteristics of the individual, the multiple hashes including the hash based on the removed data.

15. The non-transitory computer readable medium of claim 14, wherein the second instructions further cause the processor of the second server to automatically match the de-identified dataset by executing a weighting algorithm by:
generating a weight value for respective hashes of the multiple hashes;
calculating a total weight by comparing the first set of hashes to a second set of hashes associated with the previously de-identified dataset and summing the weight value for each hash of the first set of hashes that matches a hash of the second set of hashes; and identifying the match when the total weight is more than a threshold.

16. The non-transitory computer readable medium of claim 14, wherein to generate the de-identified dataset further includes generating a unique hash identifier that identifies the multiple hashes as the first set of hashes.

17. The non-transitory computer readable medium of claim 13, wherein the key value is encrypted by the remote device and transmitted to the first server by the remote device in response to user input at the remote device requesting access to a project requiring the de-identification of data.

18. The non-transitory computer readable medium of claim 13, wherein the dataset includes health data, wherein the record is a protected health information record, and wherein the individual is a health patient.

* * * * *